(12) United States Patent
Jimarez

(10) Patent No.: US 7,270,478 B2
(45) Date of Patent: Sep. 18, 2007

(54) X-RAY ALIGNMENT SYSTEM FOR FABRICATING ELECTRONIC CHIPS

(75) Inventor: Miguel Angel Jimarez, Gilbert, AZ (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 11/124,653

(22) Filed: May 9, 2005

(65) Prior Publication Data

US 2005/0194427 A1    Sep. 8, 2005

Related U.S. Application Data

(63) Continuation-in-part of application No. 10/217,920, filed on Aug. 13, 2002, now abandoned.

(51) Int. Cl.
*A61B 6/08* (2006.01)

(52) U.S. Cl. .......................... 378/205; 378/34
(58) Field of Classification Search .................. 378/34, 378/204–205, 149
See application file for complete search history.

(56) References Cited

U.S. PATENT DOCUMENTS

| | | | |
|---|---|---|---|
| 3,401,126 A | 9/1968 | Miller | |
| 3,429,040 A | 2/1969 | Miller | |
| 3,968,193 A * | 7/1976 | Langston et al. | 29/840 |
| 3,984,680 A | 10/1976 | Smith | |
| 4,016,416 A | 4/1977 | Shepherd, Jr. et al. | |
| 4,604,644 A | 8/1986 | Beckham et al. | |
| 4,614,433 A | 9/1986 | Feldman et al. | |
| 5,060,063 A | 10/1991 | Freeman | |
| 5,168,513 A | 12/1992 | Maldonado et al. | |
| 5,174,201 A | 12/1992 | Andris et al. | |
| RE34,615 E | 5/1994 | Freeman | |
| 5,735,203 A | 4/1998 | Taniguchi et al. | |
| 6,151,380 A * | 11/2000 | Zweig et al. | 378/58 |
| 6,237,218 B1 | 5/2001 | Ogawa et al. | |
| 6,272,202 B1 | 8/2001 | Chiba et al. | |
| 6,278,181 B1 | 8/2001 | Maley | |
| 6,417,573 B1 | 7/2002 | Pendse | |
| 6,492,251 B1 * | 12/2002 | Haba et al. | 438/612 |
| 2001/0026638 A1 * | 10/2001 | Sangu et al. | 382/151 |
| 2002/0146093 A1 * | 10/2002 | Williams | 378/205 |

OTHER PUBLICATIONS

Nguty et al., Correlating solder paste composition with stencil printing performance, Electronics Manufacturing Technology Symposium, 1999, Twenty-Fourth IEEE/CPMT, p. 304-312.*

* cited by examiner

*Primary Examiner*—Edward J. Glick
*Assistant Examiner*—John M Corbett
(74) *Attorney, Agent, or Firm*—George R. McGuire; Bond Schoeneck & King, PLLC

(57) ABSTRACT

A method of using x-rays to align screen printing of flip chip using x-ray sub-assembly in a chip fabricating assembly. X-rays are directed onto a substrate having receptor pads and a printing screen having fine apertures. The substrate is aligned with the printing screen based on the detection and analysis of the real-time image generated from the x-rays passing through the substrate and printing screen. The x-ray alignment system is capable of aligning gold plated receptor pads of five microns or less and disposed upon a low light contrast ceramic (e.g., 9011 alumina) substrate with a screen printing stencil having very small apertures of less than 125 microns.

9 Claims, 7 Drawing Sheets

X-RAY ALIGNMENT SYSTEM FOR FABRICATING ELECTRONIC CHIPS

CROSS-REFERENCE TO RELATED APPLICATION

The present application is a continuation-in-part of Applicant's U.S. Nonprovisional patent application Ser. No. 10/217,920, filed on Aug. 13, 2002 now abandoned.

BACKGROUND OF THE INVENTION

1. Field of Invention

This invention relates to the fabrication of electronic chips and, more particularly, to a system and method for aligning a stencil mask with the bonding pads of an electronic chip.

2. Description of Prior Art

The screen printing of solder paste with very fine pitch dimensions for the assembly of electronic (Flip) chips to chip carrier substrates is becoming more common in the art. Screen printing entails depositing a circuit pattern corresponding to that of the stencil pattern onto a chip. A chip is placed onto a positionable stage and lifted to a point just below a screen having solder paste thereon. A squeegee then moves horizontally across the screen to push solder paste through the screen to produce a stencil pattern.

Chip attachment site fiducials are commonly used for alignment of the stencil mask to the actual chip carrier substrate to be printed. As the density of chips has increased dramatically, so have the chip carrier substrates, and the attachment site fiducials cannot be added to the design because they use up too much surface area on the substrate. Indeed, special technology is needed to increase the density of contacts on the surface of the chip, and space is at a premium.

Flip chip interconnects are one way in which the density of chips is maximized. Flip chip technology involves the electrical and metallurgical joining of a chip and a carrier to form a package. The chip, or die, has an array of die pads each having a solder bump positioned thereon. These solder bumps are commonly referred to as C4s, an acronym for controlled collapse chip connection. A chip having an array of die pads and C4 bumps may be flipped over so that the C4s can be die-bonded to the contacts on a chip carrier or substrate, thereby electrically interconnecting the chip and the carrier.

In order to properly align and print C4 solder bumps onto the corresponding die pads, conventional screen printers use a vision camera, such as the Vision Probe system available from Speedline Technologies of Franklin, Mass. (formerly MPM Corporation). Such cameras, however, are limited to approximately twenty microns minimum for feature size due to the resolution of the visual imaging systems. Therefore, pads whose sizes are 5 microns or less cannot be used as alignment targets. This problem is further complicated by the fact that the commonly used ceramic substrates present very little contrast with the pads. Therefore, screen printing is only of use in conjunction with high contrast substrates or large diameter pads.

In optical alignment systems, visible light is employed to perform measurements in alignment systems. However, when finer measurements need to be made, x-ray technology can be employed. Because of their smaller wavelengths, x-rays can provide resolution beyond the limits of conventional optical parameters.

In U.S. Pat. No. 4,016,416 issued to Shepherd et al for "Phase Compensated Zone Plate Photodetector," a zone plate with a photodetector mounted on the opposite face is illustrated.

In U.S. Pat. No. 3,984,680 issued to Smith for "Soft X-Ray Mask Alignment System," an x-ray mask alignment system is illustrated featuring x-ray fluorescence detectors mounted upon the mask. The x-ray detectors measure the x-ray fluorescent signal, which provides a low intensity output as compared with an electron flux.

In U.S. Pat. No. 4,614,433 issued to Feldman for "Mask-to-Wafer Alignment Utilizing Zone Plates," a mask to-wafer alignment using zone plates illuminated by light during alignment is illustrated.

In U.S. Pat. No. 6,272,202 issued to Chiba et al on Aug. 7, 2001 for "Exposure Method and X-Ray Mask Structure for Use with the Same," an exposure method for printing circuitry onto a silicon wafer is illustrated.

In U.S. Pat. No. 6,237,218 issued to Ogawa et al on May 29, 2001 for "Method and Apparatus for Manufacturing, Multilayered Wiring Board and Multi-Layered Wiring Board," a method of using alignment marks during the lamination steps and a specialized x-ray vision and mechanical alignment machine are illustrated for fabricating printed wire boards.

In U.S. Pat. No. 5,168,513 issued to Maldonado et al on Dec. 1, 1992 for "X-Ray Metrology and Alignment Detection System," a process for aligning an x-ray mask and a work piece with an alignment mark is depicted.

In Japanese Disclosure Document No. JP05-315215 issued to Koji in 1993 for "A Semiconductor Manufacturing Apparatus," an alignment method using x-ray radiation through an aperture is shown.

In Japanese Disclosure Document No. JP62144325 issued to Shinichi on Jun. 27/1987 for "Positioning Method," the alignment of a wafer is shown using a fluorescent screen and a metal shielding x-ray pattern.

Objects and Advantages

It is a principal object and advantage of the present invention to provide an improved method and apparatus for aligning a low contrast substrate with a fine pitch printing screen having apertures of less than 125 microns.

It is another object of this invention to provide an x-ray lithography system for aligning a work piece with a fine pitch mask.

Other objects and advantages of the present invention will in part be obvious, and in part appear hereinafter.

SUMMARY OF THE INVENTION

In accordance with the present invention, a method is provided to align a screen printing stencil having very fine pitch dimensions with a chip substrate for the screen printing of solder paste onto chip carrier or substrate. The fine pitch dimensions and low light contrast of ceramics of the gold plated receptor pads on a C4 flip chip substrate prevents the use of fiducials for aligning the printing stencil. The system of the present invention comprises the replacement of a conventional optical alignment system with an x-ray sub-assembly including an x-ray generator positioned either above or below the C4 flip chip substrate and an x-ray detector positioned on the opposite side of the substrate and detector for receiving and interpreting the x-rays and generating a visual image that may be used to properly align the C4 flip chip substrate to the printing stencil. The x-ray sub-assembly is able to align the gold plated receptor pads of low contrast substrates with a screen printing stencil having apertures of less than 125 microns. The method of the present invention comprises the steps of beaming x-rays through a chip carrier substrate and associated stencil, detecting the x-rays passing through the substrate and stencil, forming a visual image of the substrate and stencil, and aligning the printing screen with the receptor pads of the substrate based on the generated image.

BRIEF DESCRIPTION OF THE DRAWINGS

The present invention will be more fully understood and appreciated by reading the following Detailed Description in conjunction with the accompanying drawings, in which.

DETAILED DESCRIPTION

Figure 1:
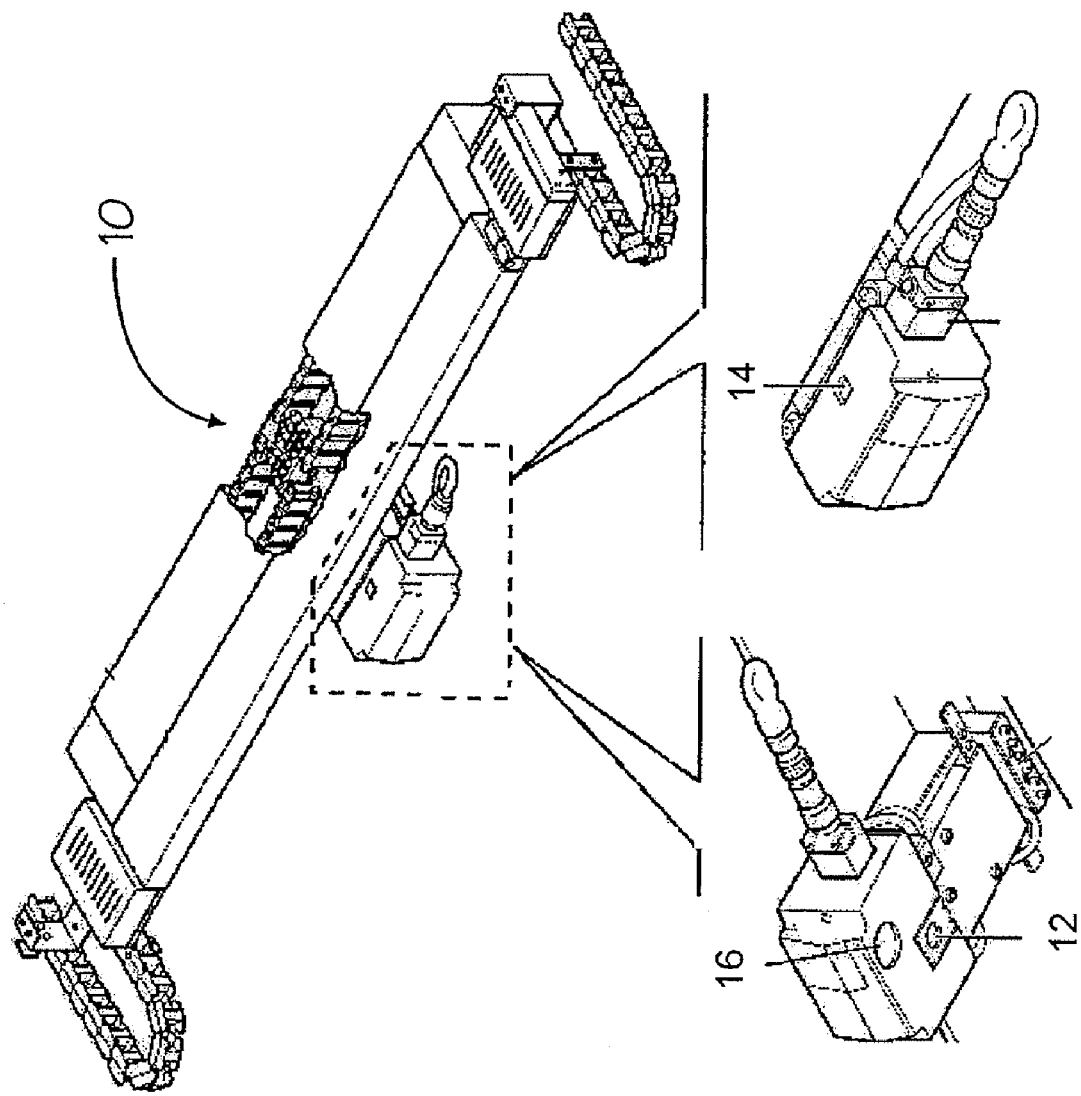
FIGS. 1a-1c are perspective views of a prior art optical imaging assembly.

Referring now to the drawing figures, wherein like numerals refer to like parts throughout, there is seen in FIG. 1 a conventional optical alignment system 10, such as Vision Probe system, for aligning a screen printing stencil with a ceramic chip carrier or substrate. Optical alignment system 10 includes illumination sources 12 and 14 positioned upwardly and downwardly, respectively, as well as a vision sensor 16, such as an optical camera for capturing a visual image of stencil 18 and substrate 22.

Figure 2:
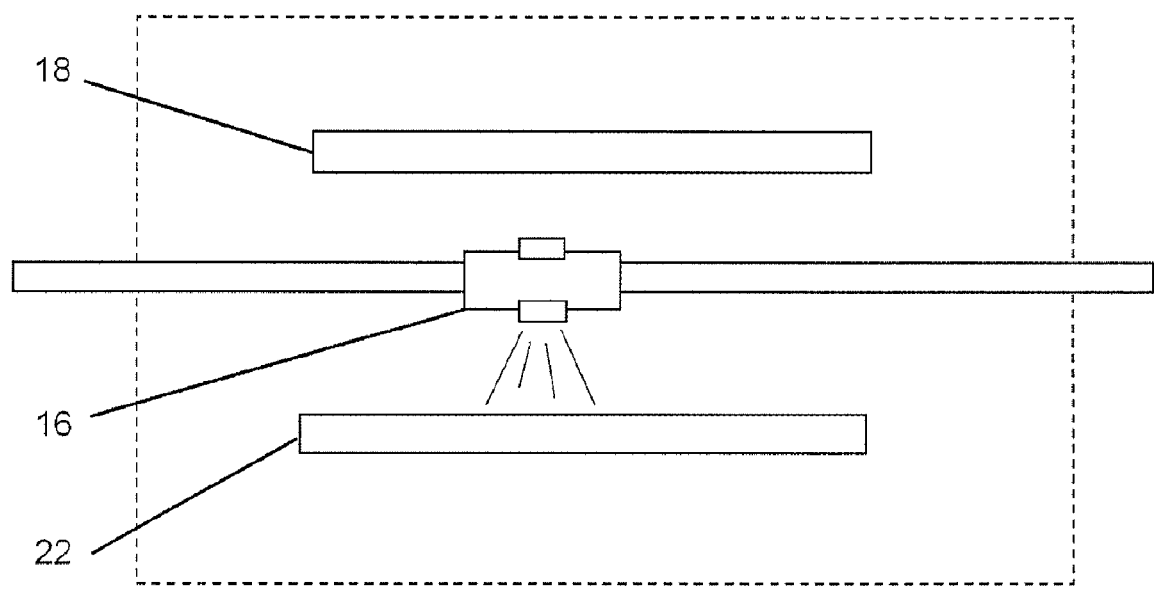
FIG. 2 is a diagram of the operation of a prior art optical imaging assembly.

Referring to FIG. 2, vision system 10 is generally positioned in screen printing machine between a stencil 18 having apertures 20 for printing solder paste and a substrate 22 having receptor pads 24 to be stenciled with solder paste. Illumination sources 12 and 14 project visible light onto stencil 18 and substrate 22, respectively, and sensor 16 detects or images the surface patterns on stencil 18 and substrate 22, respectively. The images detected by sensor 16 may be electronically stored and/or provided to a display screen (not shown) for manual alignment, or processed by a microprocessor computer for automatic alignment of stencil 18 to substrate 22 using images captured by sensor 16. Sensor 16 may be positioned on a shaft for rotation between upwardly and downwardly facing positions to image stencil 18 and substrate 22 independently, or system 10 may include a second, opposing sensor 16 to image stencil 18 and substrate 22 simultaneously.

Figure 3:
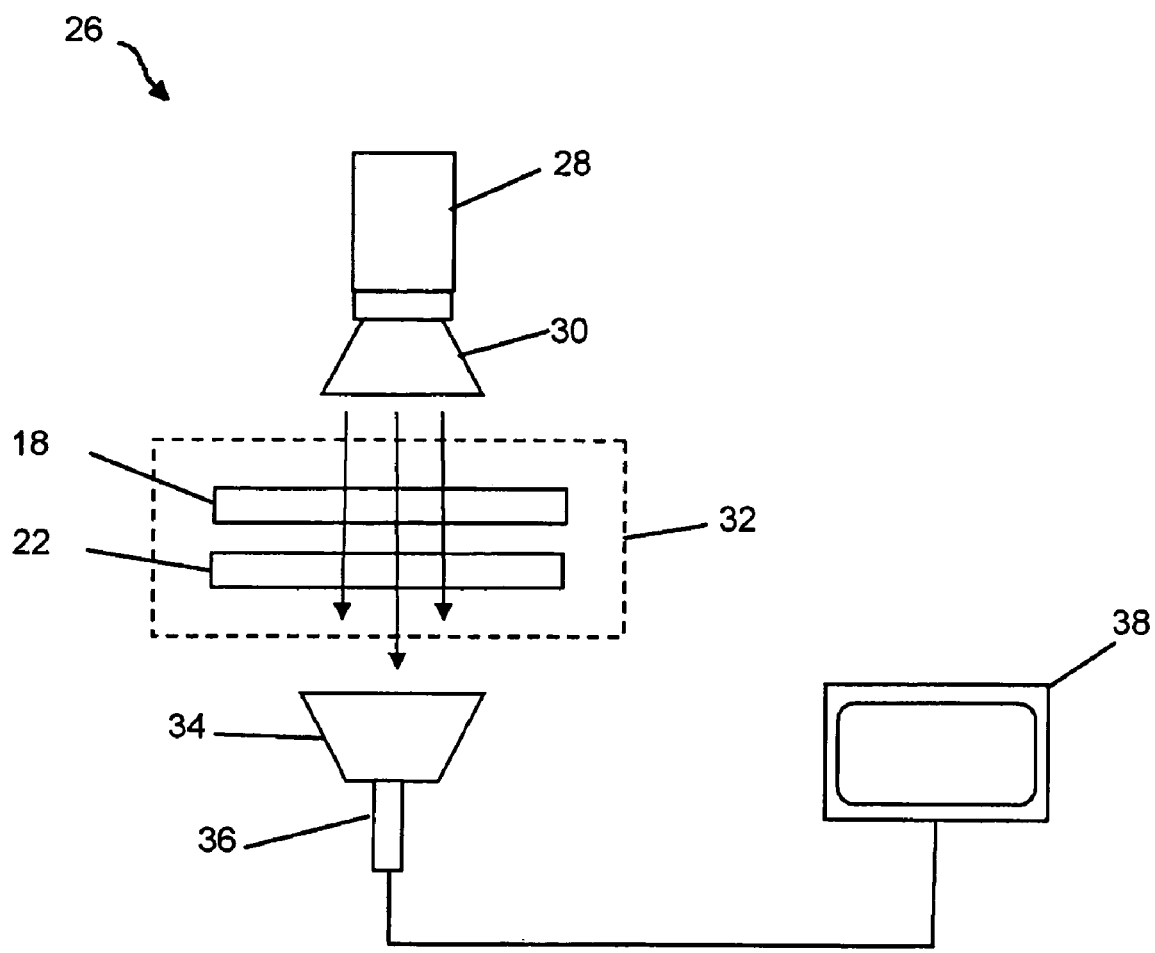
FIG. 3 is a diagram of an x-ray imaging system according to the present invention.

Referring to FIG. 3, the present invention comprises the use of a real-time x-ray system 26 in the related solder plating machine rather than optical camera system 10. X-ray system 26 generally comprises an x-ray source 28, a steering element 30, a motorized stage assembly 32, a detector 34, an x-ray sensitive camera 36, and a display screen 38. X-ray source 26 is positioned above stage 32 and generates x-rays which projected toward stage 32 and directed by steering element 30. Stage assembly 32 supports stencil 18 and substrate 22 and includes conventional structure for moving stencil 18 and/or substrate 22 in two to three dimensions (or at least relative to each other), such as microprocessor controlled carriages having side-clamping mechanisms or pins, so that apertures 20 of stencil 18 and receptor pads 24 of substrate 22 may be brought into proper alignment. X-rays from source 28 pass through stencil 18 and substrate 22 and are received by detector 34 and directed to camera 36. Camera 36 generates a real-time visual image representative of the relative positioning of apertures 20 and receptor pads 24 for display on screen 38. Stage assembly 32 may then be operated to move stencil 18 and substrate 22 relative to each other until image generated by camera 36 indicates that apertures 20 and receptor pads 24 are properly aligned for screen printing of solder paste onto receptor pads 24, thereby avoiding the need for visible fiducials. The various components for x-ray system 26 may be adapted from conventional systems used for inspecting semiconductor solder joints, such as the real-time x-ray imaging system manufactured by CR Technologies of Aliso Viejo, Calif.

Figure 4:
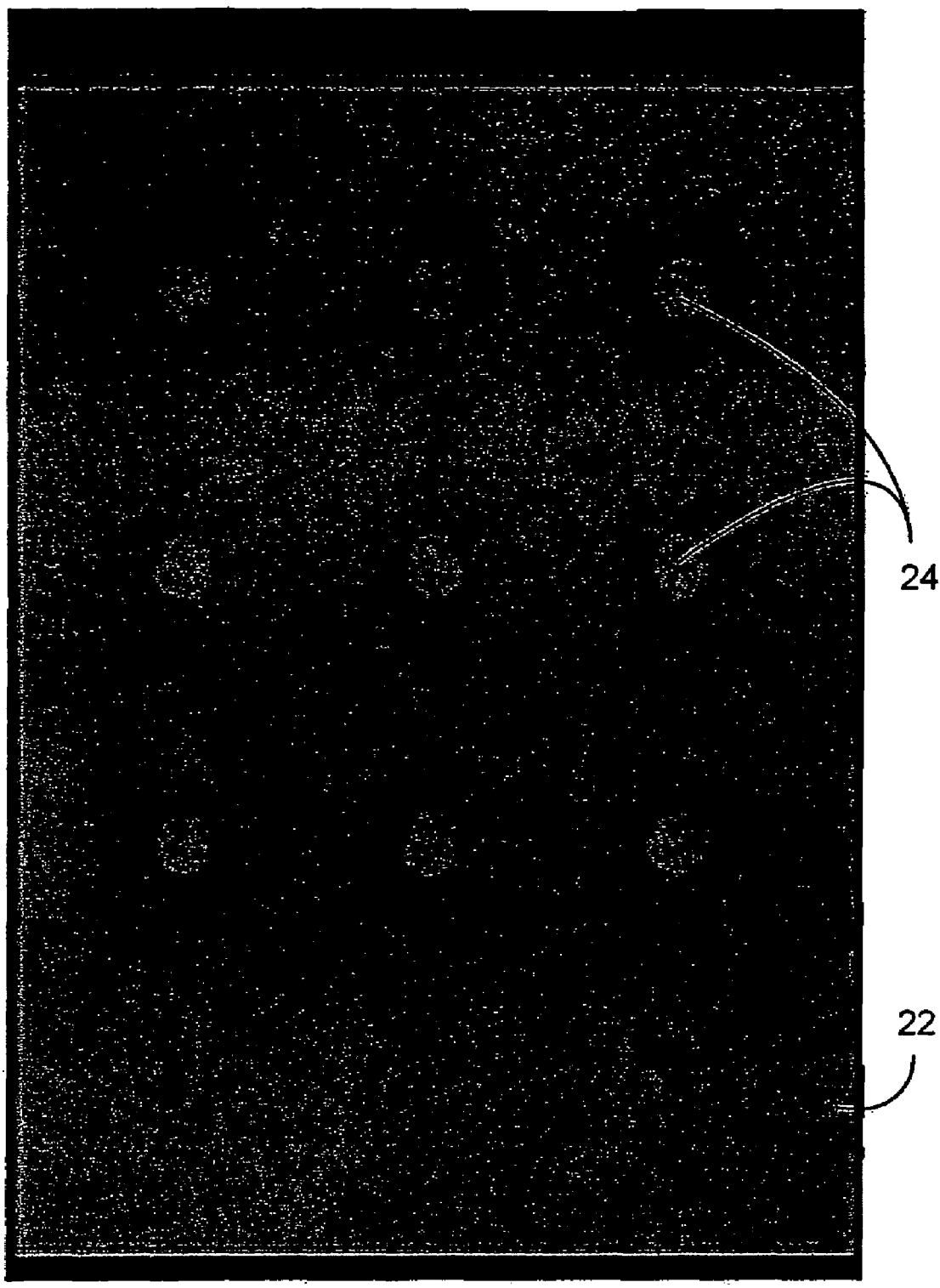
FIG. 4 is an image according to the present invention of a substrate having pads of 5 microns or less.
Figure 5:
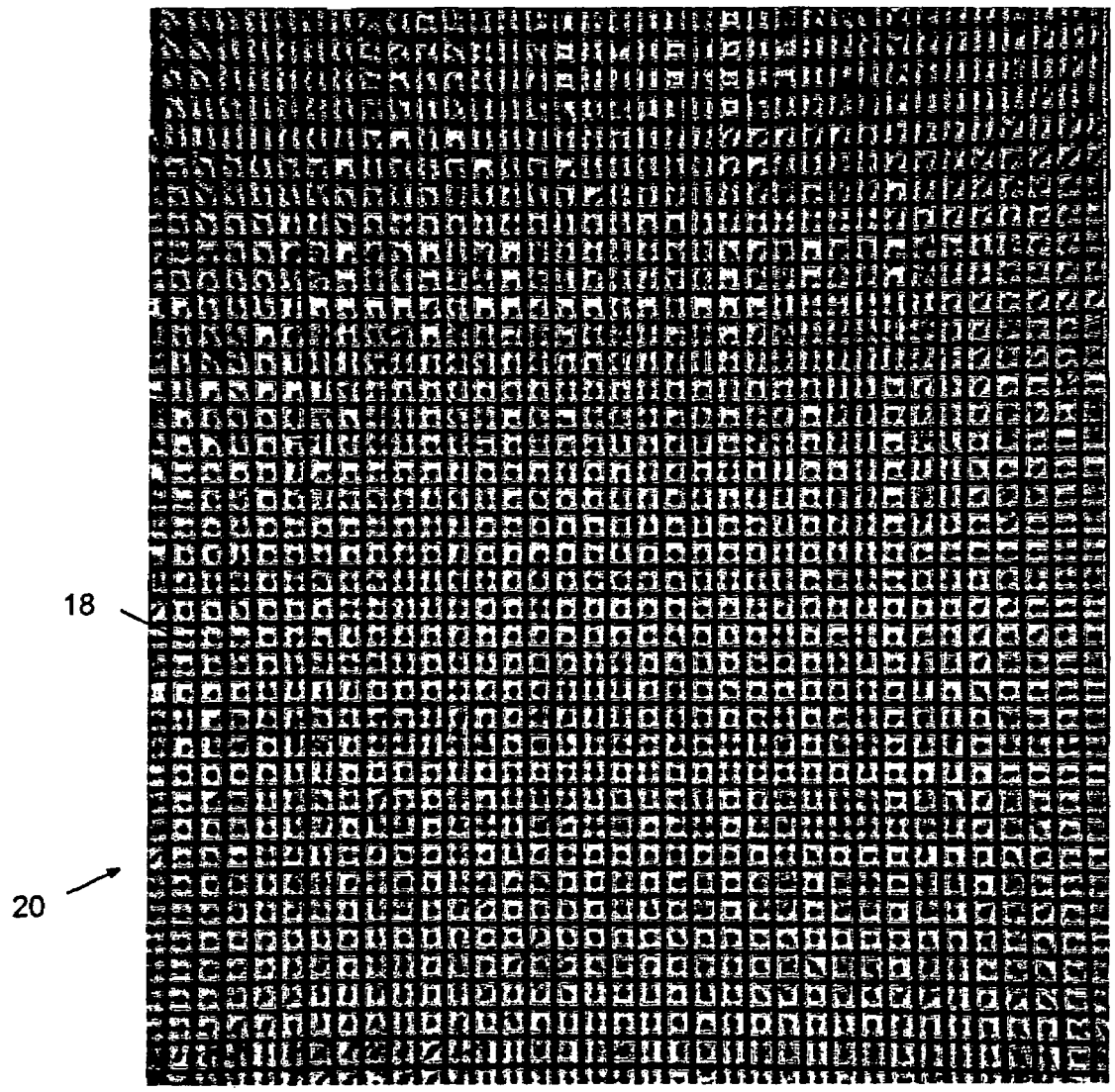
FIG. 5 is an image according to the present invention of a fine pitch stencil.
Figure 6:
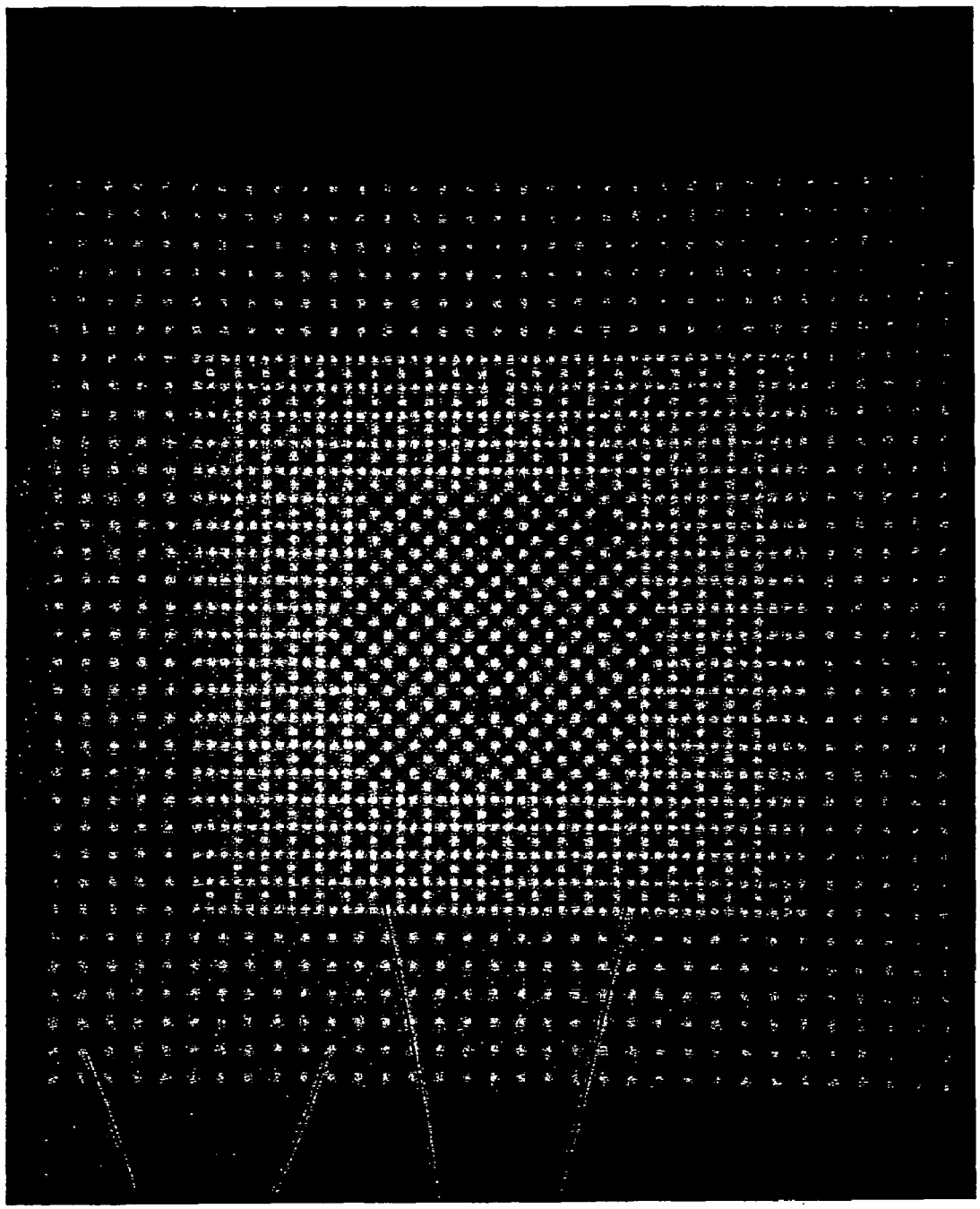
FIG. 6 is an image according to the present invention of the stencil of FIG. 5 aligned with the pads depicted in FIG. 4.

The real-time x-ray system 26 of the present invention is capable of aligning the gold plated receptor pads 24 of five microns or less disposed upon a low light contrast ceramic (9011 alumina) substrate 22, as seen in FIG. 4, with a screen printing stencil 18 having very small apertures 20 of less than 125 microns, as seen in FIG. 5. Referring to FIG. 6, apertures 20 of stencil 18 have been properly aligned with pads 24 of substrate 20 based on the visual x-ray information provided on display screen 38 so that screen printing of solder paste may commence.

Figure 7:
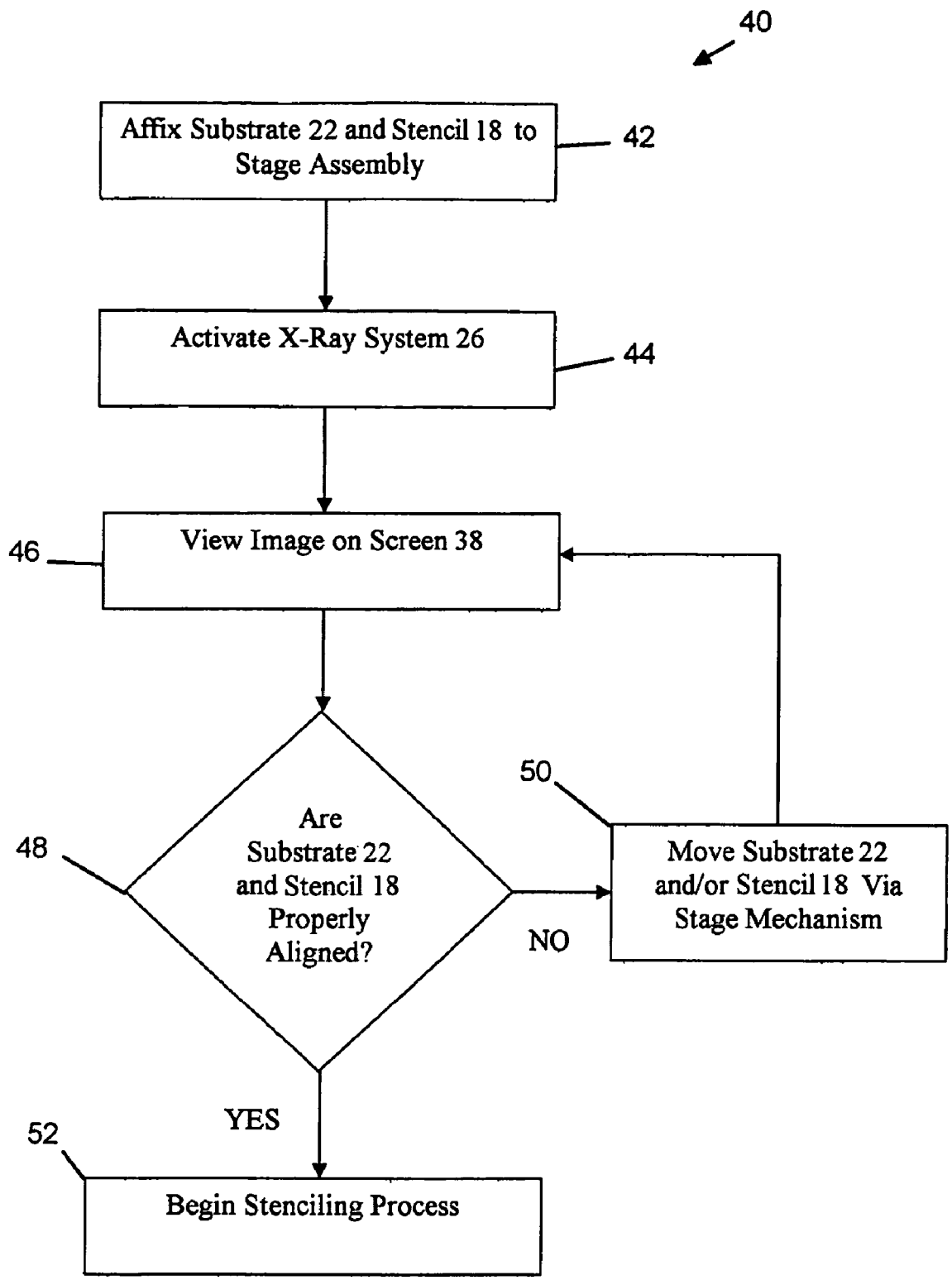
FIG. 7 is a flow chart illustrating the process associated with the present invention.

Referring to FIG. 7, the method 40 of proper alignment of stencil 18 and substrate 22 begins with the step 42 of affixing stencil 18 and substrate 22 to stage assembly 32. X-ray system 26 is then activated 44, resulting in the generating real-time images of stencil 18 and substrate 22 which may be viewed 46 on screen 38. At decisional block 48, a decision is made whether stencil 18 and substrate 22 are in proper alignment. If not, stage assembly 32 is operated 50 to move stencil 18 relative to substrate 22 and the real-time image on screen 38 is viewed and the alignment checked 48 again. If stencil 18 and substrate 22 are aligned, the screen solder printing process may begin 52. Decisional block 48 may be implemented manually by a user viewing stencil 18 and substrate 22 by then activating the appropriate moveable carriages of stage assembly 32. Decisional block 48 may also be implemented automatically by using a microprocessor that is programmed with the image processing software available in conventional visual systems and interconnected to stage assembly 32 to move stencil 18 and substrate 22 into alignment.

What is claimed is:

1. A method of aligning receptor pads of a chip substrate with apertures of printing screen, comprising the steps of:
    a) directing x-rays at said substrate and said screen;
    b) capturing x-rays that pass though said substrate and said screen;
    c) generating an image of said receptor pads of said substrate and said apertures of said screen based on said captured x-rays; and
    d) aligning said substrate relative to said screen until said generated image depicts proper alignment of said receptor pads of said substrate and said apertures of said screen.

2. The method of claim 1, wherein said printing screen is a fine pitch printing screen having apertures of less than approximately 125 microns.

3. The method of claim 1, wherein said receptor pads comprise flip chip pads.

4. The method of claim 1, wherein said receptor pads are gold plated.

5. The method of claim 1, wherein said substrate comprises ceramic.

6. The method of claim 1, wherein said receptor pads are spaced no more than approximately 5 microns from one another and said screen has a fine pitch of less than approximately 125 microns.

7. The method of claim 6, wherein said receptor pads comprise flip chip pads.

8. The method of claim 6, wherein said receptor pads are gold plated.

9. The method of claim 6, wherein said substrate comprises ceramic.

* * * * *